US008245726B2

(12) United States Patent
Mathews et al.

(10) Patent No.: US 8,245,726 B2
(45) Date of Patent: Aug. 21, 2012

(54) CITRUS JUICE APPARATUS WITH UNDESIRED MATERIAL RELEASE DETECTOR AND RELATED METHODS

(75) Inventors: Garland Mathews, Haines City, FL (US); Michael L. Suter, Lakeland, FL (US); Mark R. Jackson, Auburndale, FL (US); Kevin G. Socha, Tampa, FL (US); Jose D. Milla, Lakeland, FL (US); Gregory W. Schrader, Lakeland, FL (US)

(73) Assignee: John Bean Technologies Corporation, Chicago, IL (US)

( * ) Notice: Subject to any disclaimer, the term of this patent is extended or adjusted under 35 U.S.C. 154(b) by 755 days.

(21) Appl. No.: 11/859,232

(22) Filed: Sep. 21, 2007

(65) Prior Publication Data
US 2009/0081338 A1 Mar. 26, 2009

(51) Int. Cl.
*E03B 7/07* (2006.01)
*F16K 37/00* (2006.01)
*F17D 3/00* (2006.01)

(52) U.S. Cl. ............... 137/553; 99/513; 99/510; 99/509; 99/502; 116/70; 222/71

(58) Field of Classification Search ............ 100/37, 100/104, 107, 108, 110, 131, 134, 213, 282, 100/291; 99/495, 509, 510, 513, 451; 74/10.29, 74/10.6, 53, 54, 55, 122; 116/70, 114, 124, 116/261, 273; 137/556, 489.3, 538, 554, 137/558, 392, 393, 101.21, 553; 340/239, 340/240, 243, 366, 606, 611; 210/25, 85; 73/419, 744, 745, 746, 861.54, 861.53; 222/71
See application file for complete search history.

(56) References Cited

U.S. PATENT DOCUMENTS

| 3,442,248 | A | * | 5/1969 | Eibich et al. ............. 116/267 |
| 3,678,881 | A | * | 7/1972 | Shinn ...................... 73/28.01 |
| 4,181,835 | A | * | 1/1980 | Stadler et al. ............ 200/82 E |
| 4,665,816 | A | | 5/1987 | Waters et al. ............... 100/38 |
| 4,937,558 | A | * | 6/1990 | Robinet et al. ............ 340/606 |
| 5,193,446 | A | | 3/1993 | Olusczak et al. ........... 99/486 |
| 5,970,861 | A | | 10/1999 | Suter et al. ................. 100/37 |
| 5,996,485 | A | * | 12/1999 | Suter et al. ................. 100/37 |
| 6,375,996 | B1 | | 4/2002 | Suter et al. ............... 426/231 |
| 7,156,016 | B2 | | 1/2007 | Schrader et al. .......... 100/213 |
| 2006/0037491 | A1 | * | 2/2006 | Schrader .................. 100/213 |
| 2006/0037494 | A1 | * | 2/2006 | Schrader et al. .......... 100/213 |

FOREIGN PATENT DOCUMENTS

| CA | 1200183 | 2/1986 |
| DE | 19921777 | 11/2000 |
| EP | 0674846 | 10/1995 |

* cited by examiner

*Primary Examiner* — Henry Yuen
*Assistant Examiner* — Jianying Atkisson
(74) *Attorney, Agent, or Firm* — Allen, Dyer, Doppelt, Milbrath & Gilchrist, P.A.

(57) ABSTRACT

A citrus juice apparatus may include at least one citrus juice processing device. The at least one juice processing device may include at least one juice output having a flow of juice therethrough. The at least one juice processing device upon a malfunction may cause an undesired material release along with the flow of juice into the at least one juice output. An undesired material release detector may be coupled to the at least one juice output for detecting the undesired material release. The detector may operate based upon magnetic proximity sensing of a moving filter plate within a housing of the detector. Alternatively, the detector may operate using a filter plate, and based upon pressure.

11 Claims, 7 Drawing Sheets

CITRUS JUICE APPARATUS WITH UNDESIRED MATERIAL RELEASE DETECTOR AND RELATED METHODS

FIELD OF THE INVENTION

The present invention relates to the field of fruit processing, and, more particularly, to a citrus juice processing and associated malfunction detection.

BACKGROUND OF THE INVENTION

Citrus juice extraction on a commercial scale can be advantageously performed with a juice extractor. For example, the FMC Inline Juice Extractor manufactured by the assignee of the present invention, includes upper and lower cups that move relative to one another along a reciprocal path of travel. The sides of both the upper and lower cups typically comprise fingers that support a fruit so that it can be squeezed without bursting. The fingers of the upper cup interdigitate or intermesh with those of the lower cup.

An orange or other citrus fruit can be fed, for example, to the bottom cup by a cam-operated feeding device. The upper and lower cups are then brought together so that the respective fingers of the cup intermesh and the fruit therebetween is accordingly squeezed.

Sharp, typically circular, cutters are positioned in the top and bottom cups. As the cups move relative to one another, the fruit is pressed against the cutters. The cutters cut plugs from both the top and bottom portions of the fruit as the interdigitating fingers of the two cups mesh together.

The cutting of the plug from the top portion of the fruit promotes separation of the peel from the internal portions of the fruit (i.e., juice and pulp). The plug cut from the lower portion of the fruit allows the internal portions of the fruit to be forced down into a strainer tube positioned just below the lower cup cutter. The strainer tube, in turn, is positioned within a manifold.

After the internal portions of the fruit have been squeezed into the strainer tube, an orifice tube moves upward into the strainer tube applying pressure to the internal portion of the fruit therein. This causes the juice and juice sacs, due to their small particle size, to flow through small holes of the strainer tube and into the juice manifold, thus separating out the juice and pulp.

Further details relating to an examplary citrus juice extractor may be found in U.S. Pat. No. 7,156,016 to Schrader et al., assigned to the assignee of the present invention, and the entire contents of which are incorporated herein by reference.

When the strainer tube of the juice extractor fails, it typically will fail by tearing of the material between the holes in the wall of the strainer tube creating an enlarged opening. The unwanted opening then allows an undesired material release to contaminate the downstream processing equipment and the products produced by this equipment. The undesired material release from the extractor will typically include the core material, peel material, and seeds into the pulpy juice stream. Detection of this failure often occurs after an extended period of time causing loss of product as well as extended apparatus downtime.

Because the strainer tube is located inside the juice extractor and is not readily visible to a service person, locating the point of failure may require that each juice extracting machine on the line be partially disassembled and the strainer tubes visually inspected. As a result, the extraction process is halted until all of the extractors have been inspected to determine the failed strainer tube or tubes, and in what extractors they have failed.

A juice finisher is another type of citrus juice processing device that may typically be coupled downstream from the juice extractors. The typical juice finisher may be either a screw type finisher and/or a paddle finisher. Both types rely on the juice to be extruded through a screen material that, in turn, regulates the size of the pulp that is maintained within the juice stream. Any pulp that is too large to be extruded through the screen is compressed by centrifugal and mechanical force that is created by limiting the flow of pulp discharge either by a back pressure regulator, and/or a weighted gate. The feed rate and the pulp-to-juice ratio of the feed material may have an important effect on the level of dryness at given conditions. Feed forward control is often used based on historical data; however, another significant advance in the control of a juice finisher is disclosed in U.S. Pat. No. 6,375,996, assigned to the assignee of the present invention, and the entire contents of which are incorporated herein by reference. The patent discloses measuring pulp dryness using nuclear magnetic resonance (NMR). Based on the results of the NMR measurement, the juice injection into the finisher, the speed of the juice finisher, and/or the discharge pressure from the juice finisher is regulated.

Nevertheless, should the screen material fail or be ruptured in the juice finisher, undesired material will be released with the juice flow. In other words, the juice finisher represents another citrus processing device that when subject to malfunction may experience a release of undesired material into the juice stream. In the case of the juice finisher, the undesired material is additional pulp.

SUMMARY OF THE INVENTION

In view of the foregoing background, it is therefore an object of the present invention to provide a citrus juice apparatus and associated method that may detect an undesired material release into the juice stream.

This and other objects, features, and advantages in accordance with the present invention are provided by a citrus juice apparatus including at least one citrus juice processing device, and at least one undesired material release detector coupled thereto. More particularly, the at least one citrus juice processing device may include at least one citrus juice output having a flow of citrus juice therethrough. The at least one citrus juice processing device, upon a malfunction, may cause an undesired material release along with the flow of citrus juice into the at least one citrus juice output. For example, the at least one citrus juice processing device may comprises a citrus juice extractor including at least one strainer tube subject to failure and that upon failure may cause the undesired material release. In other embodiments, the at least one citrus processing device may comprise a juice finisher including a screen, and wherein tearing or rupture of the screen as a malfunction results in an undesired material release.

For a citrus apparatus including a plurality of citrus juice extractors, at least one detector may be associated with each extractor. Accordingly, the detector may detect which juice extractor has malfunctioned thereby permitting quick repair of the malfunctioned juice extractor, and may reduce or prevent contamination of the downstream processing equipment. In addition, a given undesired material release detector may stop the associated juice extractor based upon detecting the undesired material release.

Each citrus juice extractor may include first and second citrus juice outputs, and the associated undesired material release detector may be coupled to the first juice output, for example. The citrus juice apparatus may further comprise an undesired material release filter coupled to the second citrus juice output. The undesired material release filter may be in the form of a passive version of the undesired material release detector, that is, without the sensing components to thereby reduce costs.

The undesired material release detector may comprise a housing coupled inline with the corresponding citrus juice output, and a filter plate being movable within the housing from a normal operating position to an undesired material release position based upon the undesired material release. The detector may further comprise a sensor for sensing movement of the filter plate. The sensor may be positioned adjacent an exterior of the housing. The housing may have a greater cross-sectional area than adjacent portions of the citrus juice output. A sensor magnet may be carried by the filter plate, and the sensor may include a magnetic field sensor cooperating with the sensor magnet. The undesired material release detector may further include a pair of cooperating magnets for retaining the filter plate in the normal operating position prior to the undesired material release.

In another class of embodiments, the undesired material release detector may include a housing coupled inline with the at least one citrus juice output, and a filter plate within the housing for permitting citrus juice to flow therethrough and for impeding the undesired material release, for example. The detector may also include at least one pressure sensor for sensing at least one pressure change associated with the filter plate. The at least one pressure sensor may comprise at least one of a downstream pressure sensor, and an upstream pressure sensor relative to the filter plate.

A method aspect is for operating at least one citrus juice processing device comprising at least one juice output having a flow of citrus juice therethrough. The at least one juice processing device upon a malfunction may cause an undesired material release along with the flow of citrus juice into the at least one juice output. The method further may include detecting the undesired material release using at least one undesired material release detector coupled to the at least one citrus juice output.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
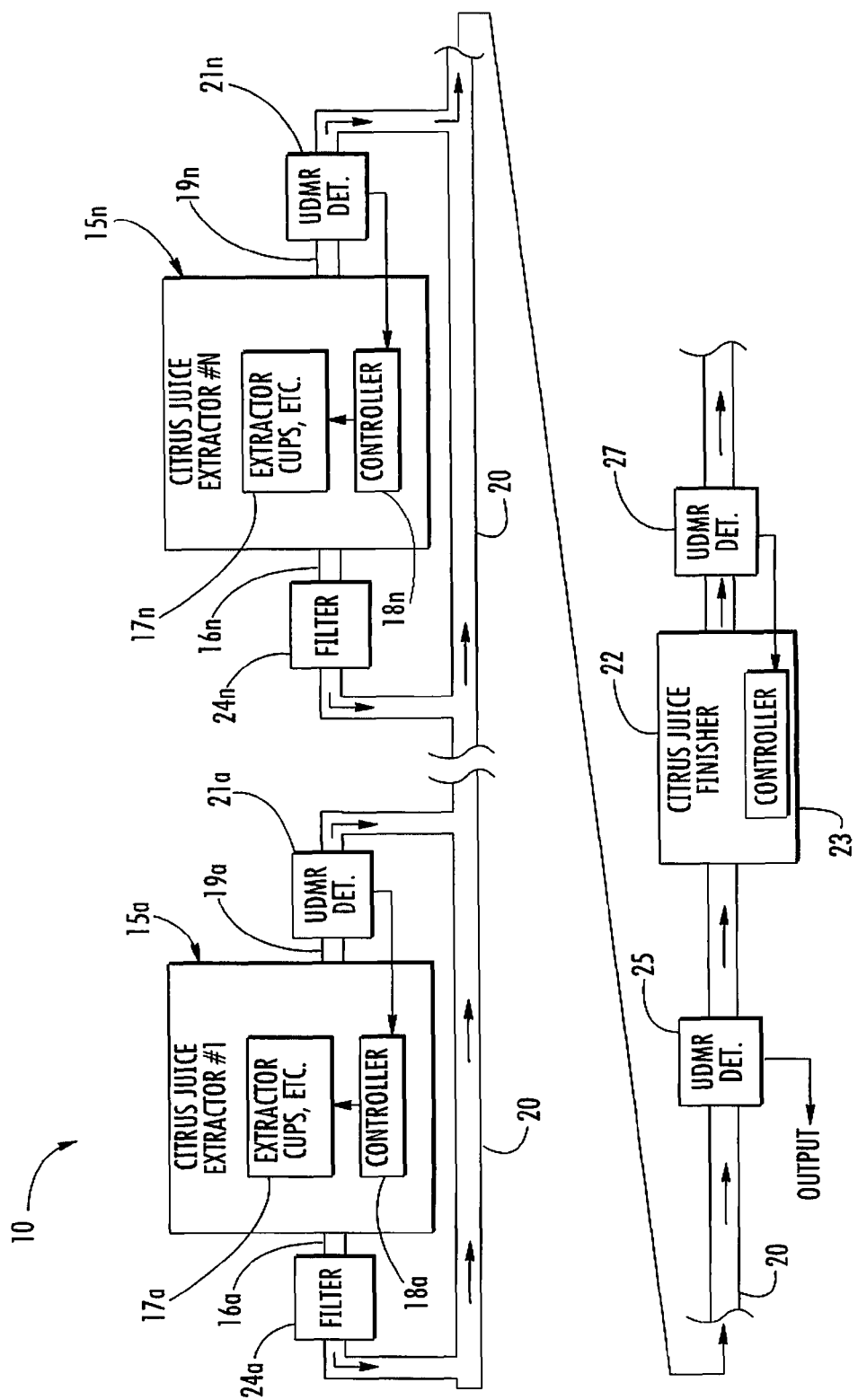
FIG. 1 is a schematic diagram of a citrus juice apparatus in accordance with the present invention.
Figure 2:
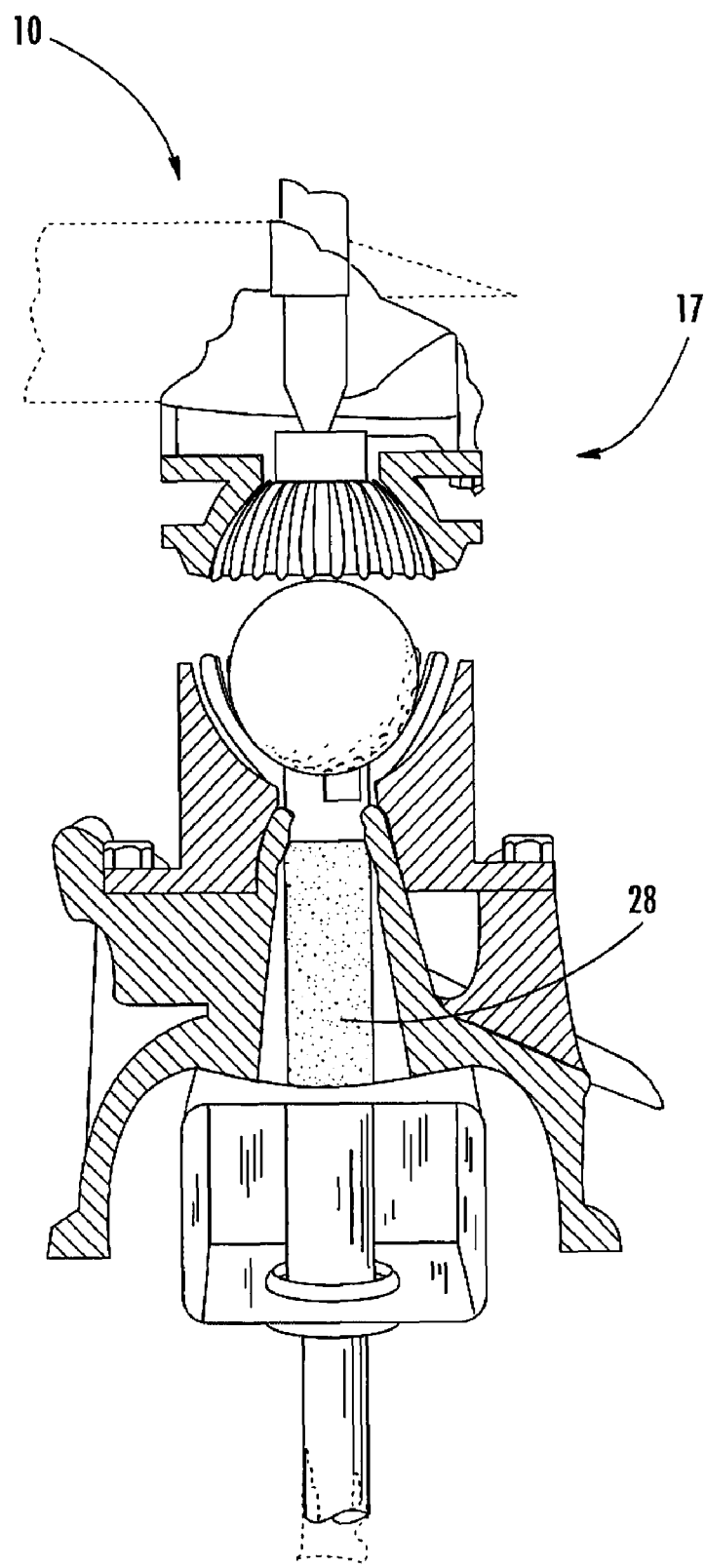
FIG. 2 is a partial cross sectional view of a portion of a juice extractor as used in a juice extractor as shown in the citrus juice apparatus of FIG. 1.

Referring initially to FIGS. 1 and 2, a citrus juice apparatus 10 is now described. The apparatus 10 illustratively comprises a plurality of N citrus juice extractors 15a-15n, each illustratively including a first juice output 16a, 16n and a second juice output 19a, 19n each having a flow of juice therethrough, and which feed into a common header 20. In other embodiments, each juice extractor 15a-15n may include only one juice output, for example, or more than two outputs, for example. Each extractor 15a-15n illustratively includes a plurality of pairs of extractor cups, and associated drive components 17a-17n operatively connected to a controller 18a-18n as will be appreciated by those skilled in the art. Further details of a representative juice extractor 15a are disclosed in the above-identified U.S. Pat. No. 7,156,016, and need no further discussion herein.

A juice finisher 22 is illustratively provided at the output of the juice header 20. Both the juice extractors 15a-15n and the juice finisher 22 are representative of citrus juice processing devices that upon malfunction cause an undesired material release into the citrus juice output. Those of skill in the art will appreciate other similar citrus juice processing devices that may benefit from the undesired material detection devices and methods described herein.

Any of the juice extractors 15a-15n, upon a malfunction, causes an undesired material release along with the flow of juice into a respective juice output. This malfunction typically occurs when the strainer tube 28 (FIG. 2) fails causing the undesired material release. A respective undesired material release (UDMR) detector 21a-21n is illustratively coupled to a first juice output 19a-19n for detecting the undesired material release. A respective detector 21a-21n is associated with each juice extractor 15a-15n and coupled to its first juice output 19a-19n. This permits identification of the failed extractor when a plurality of extractors are used, as will be appreciated by those skilled in the art. In addition, an undesired material release detector 21a-21n may also optionally send a signal to the respective controller 18a-18n of the juice extractor 15a-15n such as to stop the malfunctioning extractor.

In addition to or in place of the detectors 21a-21n for the extractors 15a-15n, an undesired material release detector 25 may be positioned downstream from all of the extractors inline with the common header 20 as shown in the bottom portion of FIG. 1. In this variation, the output from the undesired material release detector 25 may be coupled to the controllers 18a-18n of all of the extractors 15a-15n or to another control device for the group of extractors as will be appreciated by those skilled in the art.

Yet another undesired material release detector 27 is illustratively coupled downstream from the citrus juice finisher 22. The output of the detector 25 is illustratively coupled to the controller 23 of the juice finisher 22, and may shut down the finisher upon detecting an undesired release of the material. The undesired material release detector 27 for the juice finisher 22 may be used alone or in combination with any of the other detectors 21a-21n, 25 as described above.

Figure 3:
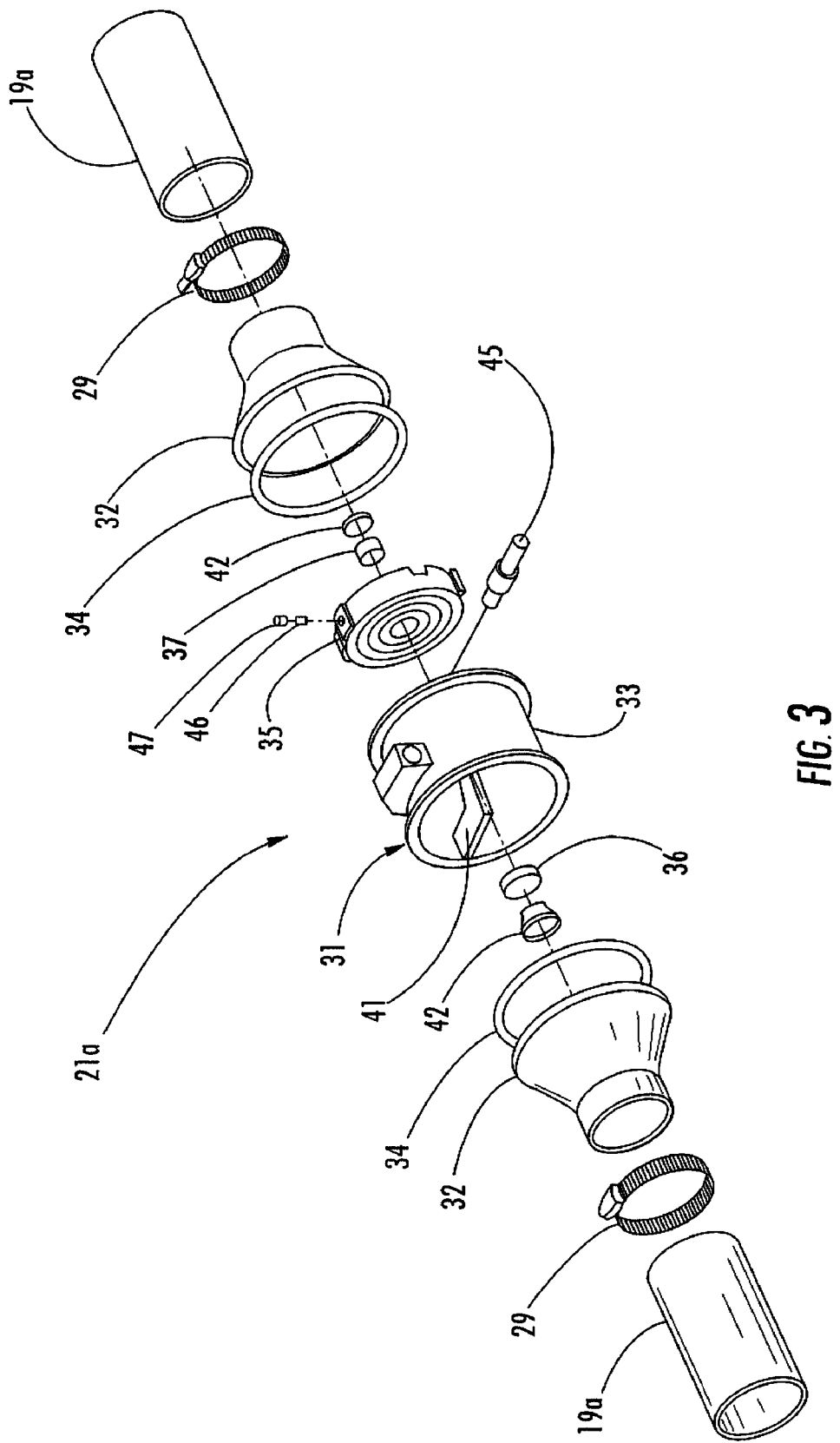
FIG. 3 is an exploded perspective view of an undesired material release detector as may be used in the citrus juice apparatus as shown in FIG. 1.
Figure 4:
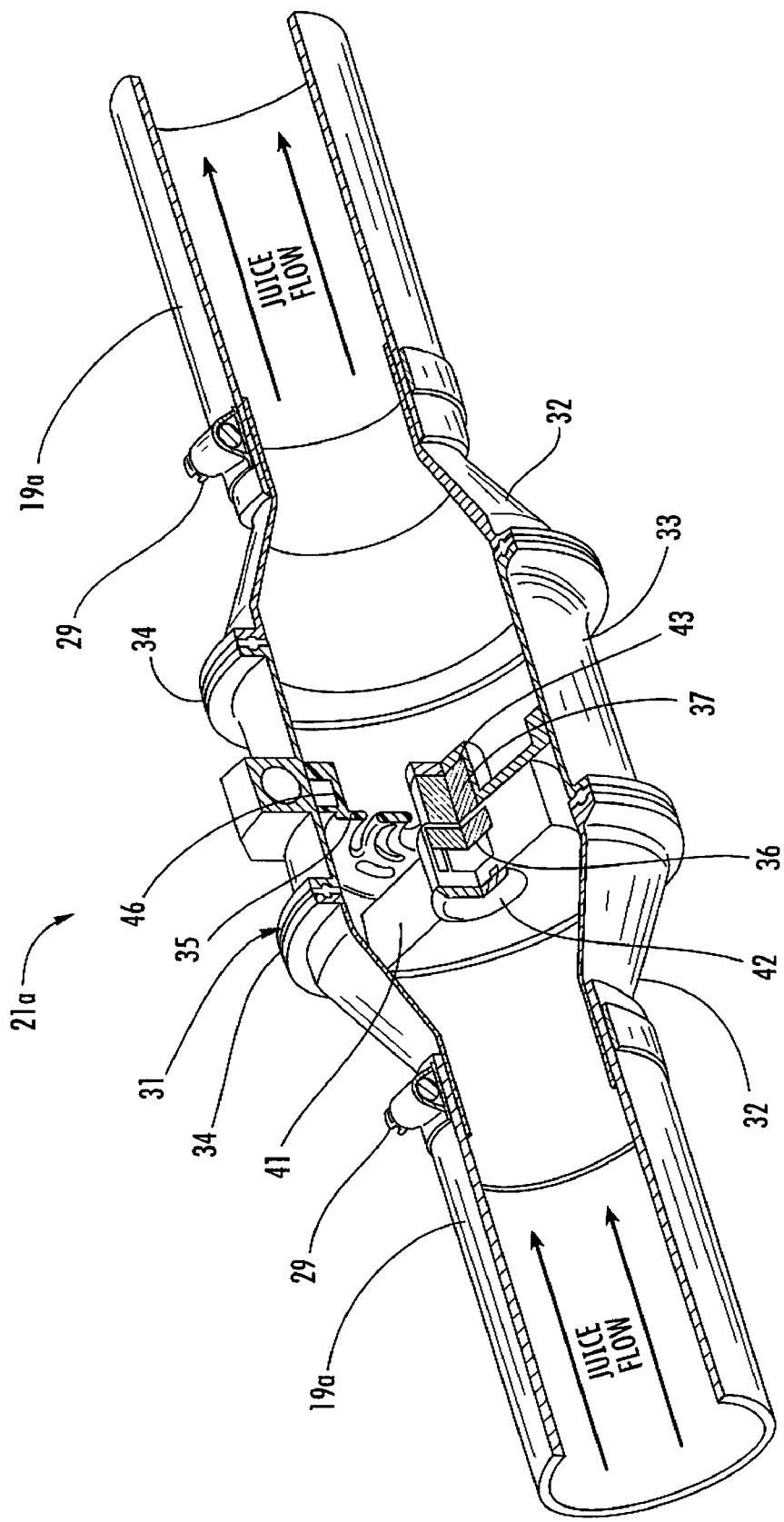
FIG. 4 is fragmentary perspective view of the undesired material release detector as shown in FIG. 3.

Turning now additionally to FIGS. 3-4, an undesired material release detector 15a illustratively includes a housing 31 coupled inline with its juice outlet 19a and secured by a pair of hose clamps 29. The housing 31 is illustratively provided by two frusto-concial end portions 32 connected to a center tubular housing portion 33. A respective sealing gasket 34 is included between the frusto-conical potions 32 and the center portion 33 to form seals therebetween. As illustrated, the housing 31, particularly at its center portion 33, also has a greater cross-sectional area than adjacent portions of the citrus juice output 19a.

A filter plate 35 is movable within the housing 31 from a normal operating position, as illustrated in FIG. 4, for example, to an undesired material release position based upon the undesired material release. Filter plate guide pins, not shown, provide a guided motion and assist a service technician in resetting the sensor plate from the undesired material release position back to the normal operating position.

The filter plate 35 illustratively includes holes and/or slots that allow the free flow of pulpy juice produced during normal operation, but yet block larger undesired material release introduced by a failed strainer tube 28, for example. Those of skill in the art will appreciate that the size and position of the filter openings will determine what material is blocked or trapped. For example, for the undesired material release detector 27 positioned downstream from the juice finisher 22 (FIG. 1), the openings may be made smaller than for the detectors 21a-21n, 25 associated with the extractors 15a-15n.

The undesired material release detector 21a further comprises first and second cooperating magnets 36, 37 for retaining the filter plate 35 in the normal operating position prior to the undesired material release. The first and second cooperating magnets 36, 37 are configured with opposite poles facing one another to attract each other in the illustrated embodiment. The first magnet 36 is illustratively coupled within a recess of an elongate mounting member 41 laterally extending across the interior of the central housing portion 33. A sealing plug 42 secures the first magnet 36 within the recess of the elongate mounting member 41. The second magnet 37 is illustratively captured within a recess at the center of the filter plate 35 by its corresponding magnet sealing plug 43.

The detector 21a also illustratively includes a magnetic field sensor 45 carried by an external portion of the housing 31 for sensing movement of the filter plate 35 within the housing based upon magnetic proximity detection. More particularly, the undesired material release detector 21a includes a sensor magnet 46 carried within an upper recess in the filter plate 35. A sensor magnet sealing plug 47 is positioned to secure the sensor magnet 46 to the filter plate 35. The magnetic field sensor 45 advantageously cooperates with the sensor magnet 46 to sense movement in the filter plate 35, and send a signal to the controller 18a, for example, such as to shut down the extractor 15a. In other words, when an undesired material release occurs, the undesired material will collect on the filter plate 35 subjecting the filter plate to a pressure as the juice flow continues until the pressure is sufficient to overcome the magnetic attractive force between the cooperating magnets 36, 37 causing the magnets to separate and the filter plate to move from the normal position. The magnetic field sensor 45 detects movement of the sensor magnet 46 as the magnet moves away from the sensor. Of course, in other embodiments, the sensor 45 could be positioned so that it detected when the magnet 46 came closer to the sensor during the undesired material release as will be appreciated by those skilled in the art. The magnetic field sensor 45 may be a magnetically operated reed switch or electronic magnetic field sensor. As will also be appreciated by those skilled in the art, other types of proximity sensing arrangements may be used including capacitive, inductive, optical, etc. In addition, contact types of sensing may also be employed.

Upon detection of an undesired material release, a service technician cleans and resets the undesired material release detector 15a. Cleaning may be accommodated by opening the housing 31 and physically removing the undesired material from the filter plate 35. The detector 15a is then reset by positioning the filter plate 35 back to the normal position where the first and second cooperating magnets 36, 37 are adjacent one another.

Figure 5:
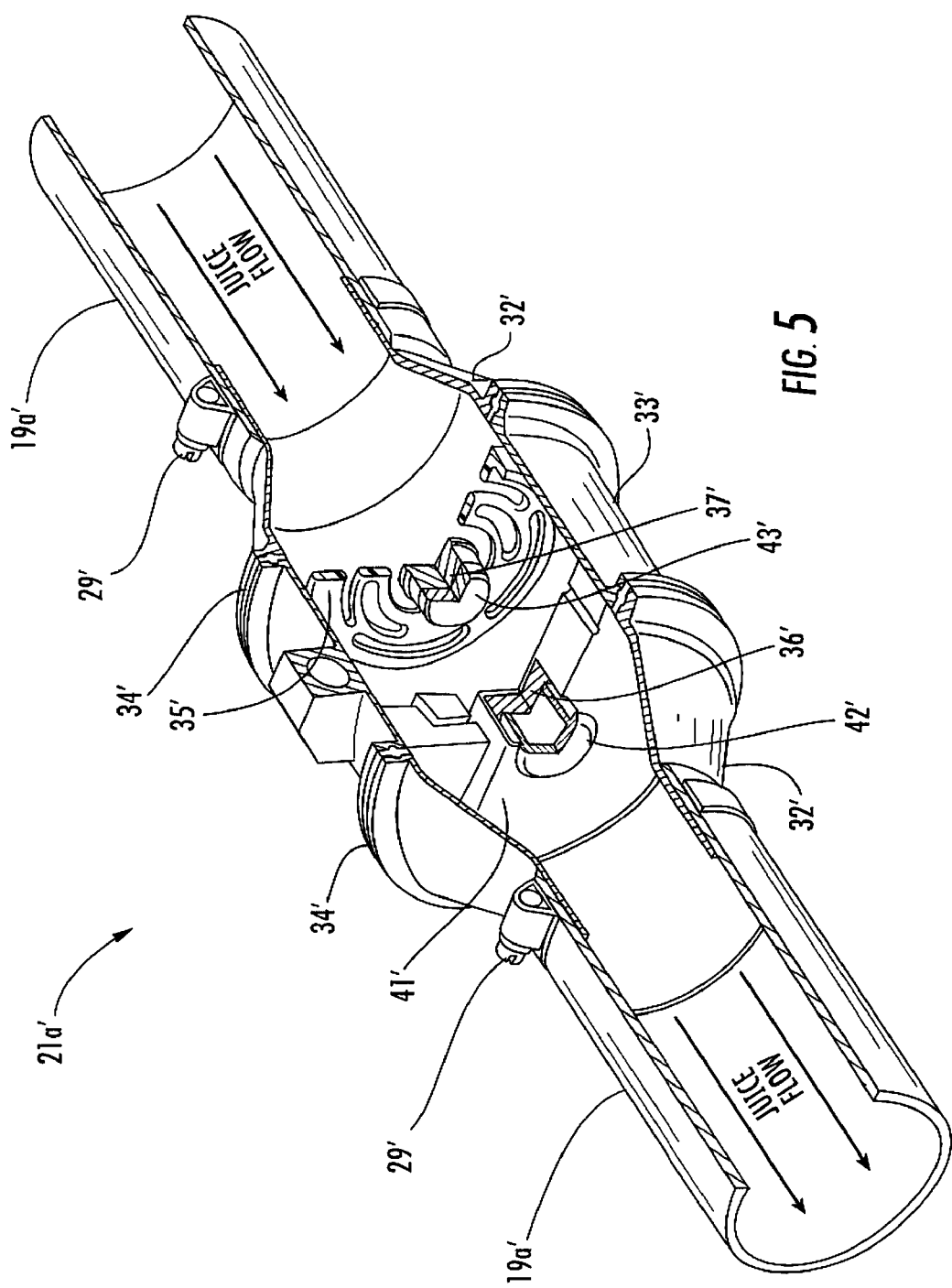
FIG. 5 is fragmentary perspective view of an alternative embodiment of an undesired material release detector as may be used in the citrus juice apparatus as shown in FIG. 1.

Referring now additionally to FIG. 5, another embodiment of an undesired material release detector 21a' is now described. In this embodiment, the first and second cooperating magnets 36', 37' are configured with like poles facing each other to thereby generate a repelling force when the filter plate 35' is in the normal position. Accordingly, the filter plate 35' is movable within the housing 31' from the normal operating position, where cooperating first and second magnets 36', 37' are spatially separated, to an undesired material release position where the magnets are urged closer together based upon the undesired material release as will be appreciated by those skilled in the art. This embodiment may lend itself to easier cleaning and resetting because the filter plate 35' is spaced from the elongate member 41' and the magnet 36' carried thereby in the normal position.

Figure 6:
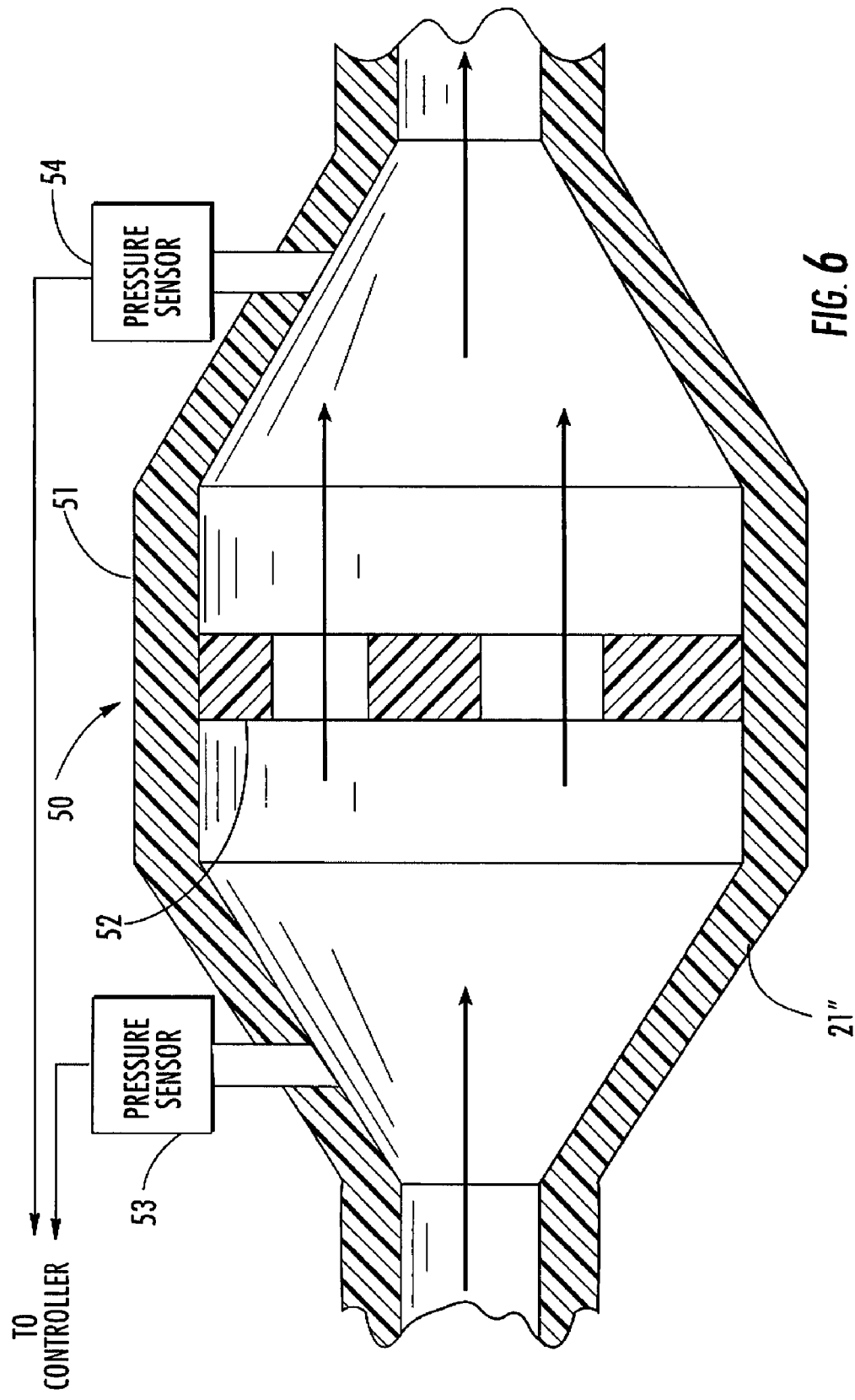
FIG. 6 is a schematic cross-sectional view of yet another embodiment of an undesired material release detector as may be used in the citrus juice apparatus as shown in FIG. 1.

Turning now to FIG. 6, yet another embodiment of an undesired material release detector 50 is now described. The undesired material release detector 50 illustratively includes a housing 51 to be coupled inline with a citrus juice output from any of the citrus processing devices described above, for example. A filter plate 52 is positioned within the housing 51 for permitting juice to flow therethrough and for impeding the undesired material release. An upstream pressure sensor 53, and a downstream pressure sensor 54, relative to the filter plate 52, are illustratively coupled to the housing 51. Electrical signal outputs from each pressure sensor 53, 54 may be coupled to a controller to control operation of the associated citrus processing device. As will be appreciated by those skilled in the art, a sensed differential pressure across the filter plate 51 provides an indication of the undesired material release. Of course, in some embodiments only a single pressure sensor or pressure transducer may be needed to sense the pressure change associated with the undesired material release.

Returning again to the extractor or top portion of FIG. 1, an alternative to having a second undesired material release detector on each of the second extractor outputs 16a-16n is the provision of an undesired material release filter 24a-24n on these second outputs. The undesired material release filters 24a-24n may be considered as passive versions of the detectors 21a-21n. In other words, the filter plate 35 may be in a fixed position within the housing 31 and no sensing components need to be included. Of course, the other undesired material release detector embodiments 21a' (FIG. 5) and 50 (FIG. 6) may be similarly modified to produce a passive undesired material release filter as will be appreciated by those skilled in the art. Accordingly, the structure of such filters requires no further discussion herein.

An undesired material release filter 24a-24n will trap the undesired material release from further propagation. Moreover, the substitution of the undesired release material release filters 24a-24n instead of the detectors, provides a lower cost for the same protection for the apparatus embodiment 10 as shown in the illustrated embodiment, where each extractor 15a-15n includes two outputs 16a, 16n, 19a, 19n. In embodiments where each of the juice extractors 15a-15n has only one juice output, the undesired material release filter does not have to be included as will also be appreciated by those skilled in the art.

Figure 7:
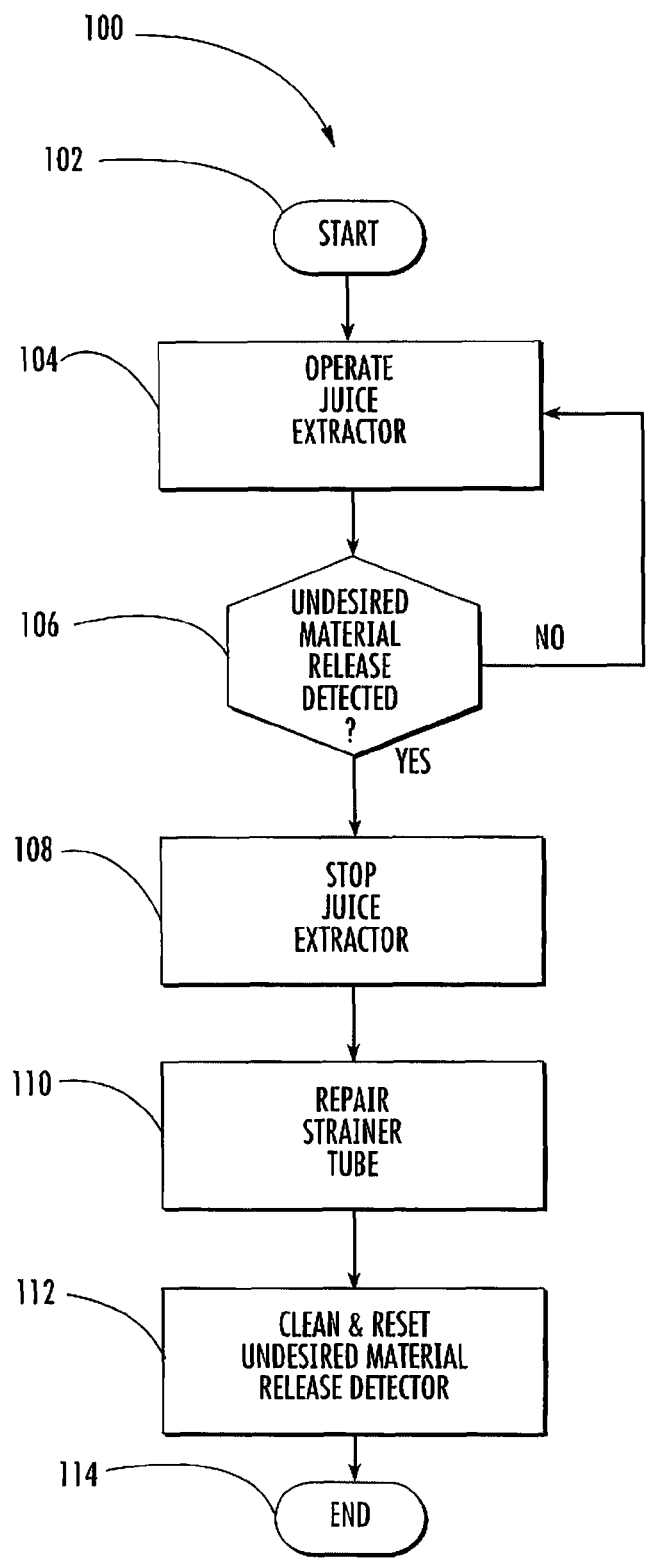
FIG. 7 is a flow chart of a method of juice extraction in accordance with the present invention.

Now referring to the flowchart 100 of FIG. 7, a method of juice extraction is now described. Beginning at Block 102, the method includes operating a juice extractor comprising at least one juice output having a flow of citrus juice therethrough (Block 104). Upon a malfunction the juice extractor causes an undesired material release along with the flow of juice into the juice output. Accordingly, the method includes detecting the undesired material release using an undesired material release detector coupled to the juice output (Block 106). The undesired material release may be detected, for example, based upon detecting movement of the filter plate in relation to the magnetic field sensor as described above, or may be detected by a change in pressure as also described above. In the illustrated embodiment, at Block 108 the undesired material release detector may also stop the juice extractor by sending a signal to the controller when an undesired material release has been detected.

Once an undesired material release has been detected, a service person will then repair the extractor, typically by replacing the strainer tube (Block 110). The service person will then typically clean and reset the undesired material release detector at Block 112 before stopping at Block 114. Those of skill in the art will appreciate a similar operating sequence for the undesired material release detector 25 coupled to the header 20 of the apparatus 10 as shown in FIG. 1, and a similar operating sequence for the undesired material release detector 27 coupled to the juice finisher 27.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A citrus juice apparatus comprising:
a plurality of citrus juice processing extractors each comprising at least one citrus juice output having a flow of citrus juice therethrough;
each of said plurality of citrus juice processing extractors upon a malfunction thereof causing an undesired material release along with the flow of citrus juice into said at least one citrus juice output; and
at least one undesired material release detector being associated with each of said plurality of citrus juice processing extractors and being coupled to the at least one citrus juice output of each of said plurality of citrus juice processing extractors for detecting the undesired material release, said at least one undesired material release detector comprising
a housing coupled inline with said at least one citrus juice output,
a filter plate being movable within said housing from a normal operating position to an undesired release position based upon the undesired material release, and
a sensor for sensing movement of said filter plate.

2. The citrus juice apparatus according to claim 1 wherein a given undesired material release detector stops an associated citrus juice extractor based upon detecting the undesired material release.

3. The citrus juice apparatus according to claim 1 wherein each citrus juice extractor comprises first and second citrus juice outputs; wherein the associated undesired material release detector is coupled to the first citrus juice output; and further comprising an undesired material release filter coupled to the second citrus juice output.

4. The citrus juice apparatus according to claim 1 wherein said sensor is positioned adjacent an exterior of said housing.

5. The citrus juice apparatus according to claim 1 wherein said housing has a greater cross-sectional area than adjacent portions of said at least one citrus juice output.

6. The citrus juice apparatus according to claim 1 further comprising a sensor magnet carried by said filter plate; and wherein said sensor comprises a magnetic field sensor cooperating with said sensor magnet.

7. The citrus juice apparatus according to claim 1 wherein said at least one undesired material release detector further comprises a pair of cooperating magnets for retaining said filter plate in the normal operating position prior to undesired material release.

8. A citrus juice apparatus comprising:
a plurality of citrus juice processing extractors each comprising at least one citrus juice output having a flow of citrus juice therethrough;
each of said plurality of citrus juice processing extractors upon a malfunction thereof causing an undesired material release along with the flow of citrus juice into said at least one citrus juice output; and
at least one undesired material release detector being associated with each of said plurality of citrus juice processing extractors and being coupled to the at least one citrus juice output of each of said plurality of citrus juice processing extractors for detecting the undesired material release, said at least one undesired material release detector comprising
a housing coupled inline with said at least one citrus juice output,
a filter plate within said housing for permitting citrus juice to flow therethrough and for impeding the undesired material release, and
at least one pressure sensor for sensing at least one pressure change associated with said filter plate.

9. The citrus juice extracting apparatus according to claim 8 wherein said at least one pressure sensor comprises at least one of a downstream pressure sensor and an upstream pressure sensor relative to said filter plate.

10. The citrus juice apparatus according to claim 8 wherein a given undesired material release detector stops an associated citrus juice extractor based upon detecting the undesired material release.

11. The citrus juice apparatus according to claim 8 wherein each citrus juice extractor comprises first and second citrus juice outputs; wherein the associated undesired material release detector is coupled to the first citrus juice output; and further comprising an undesired material release filter coupled to the second citrus juice output.

* * * * *